(12) United States Patent
Pfeiffer

(10) Patent No.: US 7,815,799 B2
(45) Date of Patent: Oct. 19, 2010

(54) CONTINUOUS COUNTERCURRENT CHROMATOGRAPHY SYSTEM

(76) Inventor: Nikolaus Stephan Pfeiffer, Humboldtstrasse 12, Langenau (DE) D-89129

( * ) Notice: Subject to any disclaimer, the term of this patent is extended or adjusted under 35 U.S.C. 154(b) by 114 days.

(21) Appl. No.: 12/304,869

(22) PCT Filed: May 14, 2007

(86) PCT No.: PCT/DE2007/000877

§ 371 (c)(1),
(2), (4) Date: Dec. 15, 2008

(87) PCT Pub. No.: WO2007/143963

PCT Pub. Date: Dec. 21, 2007

(65) Prior Publication Data

US 2009/0173680 A1    Jul. 9, 2009

(30) Foreign Application Priority Data

Jun. 15, 2006  (DE) ........................ 10 2006 028 129

(51) Int. Cl.
*B01D 15/08*   (2006.01)
(52) U.S. Cl. .................... 210/198.2; 210/635; 210/657
(58) Field of Classification Search ................. 210/635, 210/656, 657, 198.2
See application file for complete search history.

(56) References Cited

U.S. PATENT DOCUMENTS

| | | | | |
|---|---|---|---|---|
| 3,775,309 A * | 11/1973 | Ito | ............................ | 210/635 |
| 4,051,025 A * | 9/1977 | Ito | ............................ | 210/635 |
| 4,551,251 A * | 11/1985 | Kolobow et al. | ............ | 210/635 |
| 4,857,187 A * | 8/1989 | Ito | .......................... | 210/198.2 |
| 4,968,428 A * | 11/1990 | Nunogaki | .................... | 210/635 |
| 6,537,452 B1 * | 3/2003 | de La Poype et al. | .... | 210/198.2 |
| 6,913,692 B2 * | 7/2005 | Margraff et al. | ......... | 210/198.2 |
| 7,422,685 B2 * | 9/2008 | Couillard et al. | ......... | 210/198.2 |
| 2004/0173534 A1 * | 9/2004 | Margraff et al. | ............ | 210/656 |

* cited by examiner

*Primary Examiner*—Ernest G Therkorn
(74) *Attorney, Agent, or Firm*—Laurence A Greenberg; Werner H Stemer; Ralph E Locher

(57) ABSTRACT

A continuous countercurrent chromatography system has several rotating chambers arranged around a rotational axis. The chambers are provided for receiving a liquid or liquid mixture to be examined, and the individual chambers are interconnected via liquid carrying connections in such a way as to relay two liquids in countercurrent, wherein one liquid first passes through several chambers and is then returned to the chambers first traversed.

13 Claims, 2 Drawing Sheets

CONTINUOUS COUNTERCURRENT CHROMATOGRAPHY SYSTEM

REFERENCE TO RELATED APPLICATIONS

This application is a 371 of PCT/DE2007/000877 filed May 14, 2007.

BACKGROUND OF THE INVENTION

Field of the Invention

The invention relates to a continuous countercurrent chromatography system for separating and/or cleaning substances according to the principle of liquid-liquid distribution.

The principle of liquid-liquid distribution has existed for many years already, but it involves batch operation, i.e., only a small sample quantity can be charged. The next sample quantity can only be charged after the preceding one has gone through the entire process. Such an arrangement is known from WO 2004/079363 A, wherein a phase is relayed through several chambers rotating on a cylindrical periphery.

BRIEF SUMMARY OF THE INVENTION

The object of the invention is to provide a chromatography system improved relative to prior art, which enables an efficient, continuous material separation.

This object is achieved by a continuous countercurrent chromatography system according to the claimed features of claim 1.

The invention proposes a continuous countercurrent chromatography system with several rotating chambers arranged around a rotational axis, wherein the chambers are provided for accommodating a liquid to be examined or a liquid mixture, wherein the individual chambers are interconnected via liquid-conducting connections in such a way as to carry two liquids in countercurrent, wherein one liquid first passes through several chambers and then returns to preceding chambers to reach a concurrent flow.

The proposed continuous countercurrent chromatography system is here characterized in that it exhibits a good separation effect as well as a good productivity for an efficient thorough mixing and subsequent segregation of the phases.

The sample substance supplied to the liquids is optimally separated by solubility in this way. The sample substance can here of course also be a mixture of various materials. By comparison to prior art, this makes it possible for the first time to partially recycle the sample while the process is ongoing.

One especially preferred embodiment of the invention provides that a liquid mixture be supplied to the chambers on a side of a chamber lying near the rotational axes after taken from a chamber lying adjacently opposite the rotational direction at its side remote from the rotational axes.

One also especially preferred embodiment of the invention provides that a liquid mixture be supplied to chambers of a first group on a side remote from the rotational axes after taken from a next but one chamber in the rotational direction at its side near the rotational axes.

Another especially preferred embodiment provides that a liquid mixture be supplied to chambers in a second group on a side remote from the rotational axes after taken from a chamber lying adjacently opposite the rotational direction at its side near the rotational axes.

It is advantageously provided that the removal sites and supply sites of a chamber each lie on a radial.

A further development provides that the two liquids or liquid mixtures consist of a heavy phase on the one hand and a light phase on the other.

The chambers are advantageously interconnected to form an uninterrupted ring.

The two liquids are advantageously each supplied to an access site to the interconnected chambers.

An especially advantageous further development of the invention provides that a sample substance be supplied between these access sites at another point of the interconnected chambers forming a chain.

One variant proposes that the mixtures be immiscible.

The liquid or liquid mixture is preferably a solvent or solvent mixture for the sample substance.

In an especially effective structural design, it is provided that the chambers be situated in a circle.

The chambers are advantageously identical in structural design.

The invention will be described in more detail below based on the drawings. The schematics show:

DESCRIPTION OF THE INVENTION

The identical reference numbers in the figures denote elements that are the same or have the same effect.

Figure 1:
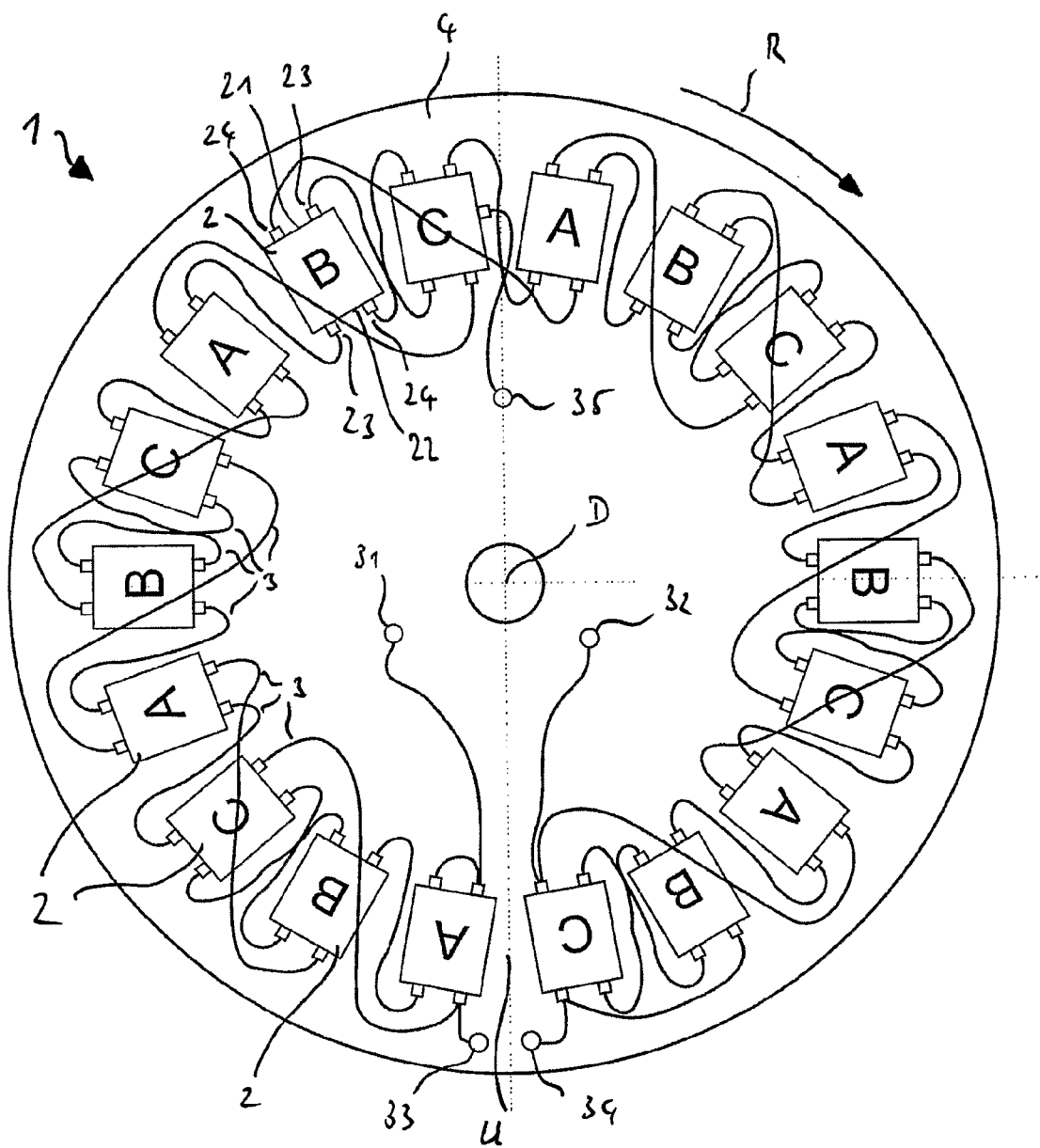
FIG. 1 A diagrammatic top view of a continuous countercurrent chromatographic system according to the invention, FIG. 2 A diagrammatic view of three exemplary chambers, wherein the flow is indicated explanatorily, and FIG. 3 A diagrammatic view of the result of separating the phases of the three chambers from FIG. 2, which is achieved by traversing the chambers from left to right.

FIG. 1 shows a diagrammatic view of a continuous countercurrent chromatography device 1 according to the invention with several chambers 2 arranged around a rotational axis D and rotating in direction R. The chambers are interconnected via liquid-carrying connections 3.

A liquid or liquid mixture to be examined flows through the connected chambers 2.

After flowing through several chambers, the liquid is returned to preceding chambers in countercurrent by the layout of the lines, as a result of which concurrent flow is achieved in the chambers.

The chambers 2 are arranged in a circle on a carrier plate 4 that rotates around the rotational axis D, wherein the chambers 2 are interconnected to form an uninterrupted ring by the lines 3.

The removal sites 23 and supply sites 24 of a chamber each lie on a radial relative to their arrangement around the rotational axis D.

At the interruption U of the ring, the two liquids are continuously supplied to a respective inlet 31, 32, 33, 34 to the interconnected chambers, and the separated liquids are removed.

The liquid or liquid mixture itself is a solvent for the sample substance. The latter is supplied to the connected chambers 2 forming a chain between these inlets at a feed inlet 35.

Figure 2:
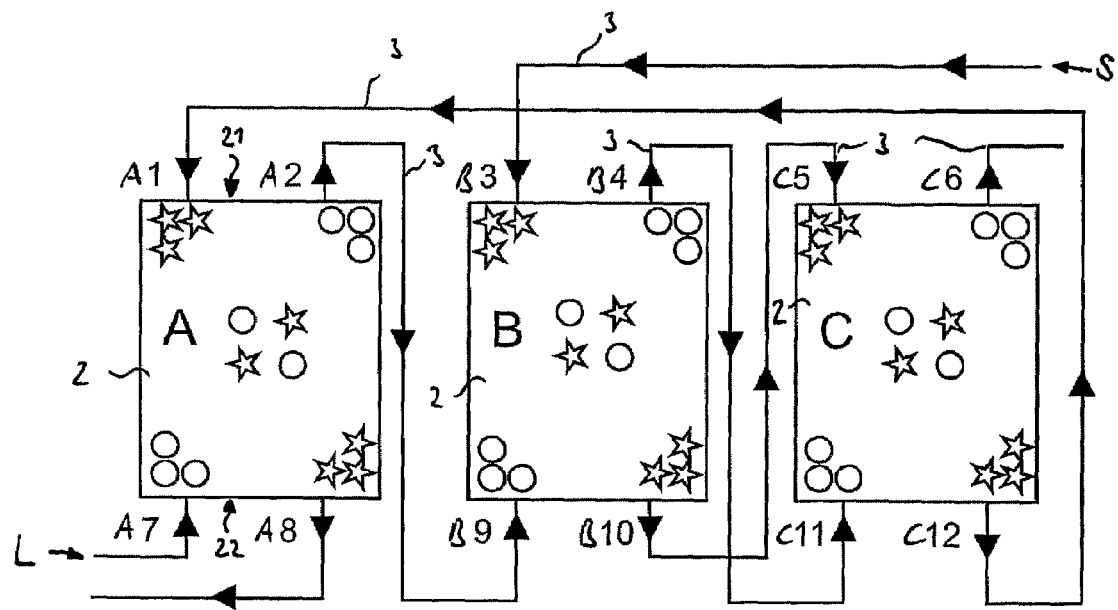

FIG. 2 shows another diagrammatic view of how the liquid is guided. A liquid mixture is supplied to the chambers A; B; C on a side 22 of a chamber B; C; A near the rotational axes, after removed at a chamber A; B; C lying adjacently opposite the rotational direction on its side 21 remote from the rotational axes.

A liquid mixture is supplied to the chambers A; B (first group) at a side 21 remote from the rotational axes, after removed at a next but one chamber C; A in the rotational direction at its side 22 near the rotational axes.

A liquid mixture is supplied to the chambers C (second group) at a side 21 remote from the rotational axes, after removed at a chamber (B) lying adjacently opposite the rotational direction on its side 22 near the rotational axes.

The two liquids or liquid mixtures are comprised of a heavy phase on the one hand and a light phase on the other. This improves the separation of the sample substance.

One phase L is supplied to chamber A via terminal A7, to chamber B via terminal A2 and B9, and to chamber C via terminal B4 and C11.

Phase L is then supplied to chamber A of terminal A7 of the right adjacent block via terminal C6 from other chambers A, B, C (not shown).

Phase S is supplied from a corresponding terminal A8 of chamber A of the adjacent block (not shown) to chamber B of terminal B3.

Via terminal B10 and C5 to chamber C of terminal C11, and from there via terminal C12 and A1 to chamber A. From there, phase S is supplied via terminal A8 to terminal B3 of the left block (not shown) B.

The plurality of interconnected chambers makes it possible to relay two in particular immiscible liquids in countercurrent. The phases are thoroughly mixed in the chambers, thereby dividing a third sample substance into the respective phases based on its solubility. Use is here made of the spherical separating funnel principle and Nernst distribution.

The forced rotation generates a centrifugal force in the chambers, thereby yielding a separation of phases in the same chamber, so that the phases can be routed to the next chamber separated.

Since the rapid thorough mixing and segregation, and hence defined relaying of respectively pure phases L and S cannot be realized in countercurrent, the phases are carried in crosscurrent in the individual chambers. These chambers are combined into blocks (e.g., chamber A, B, C) via a special array of connections, and the phases are relayed concurrently in these blocks. The countercurrent process is achieved by the layout of connections between the individual blocks.

Figure 3:
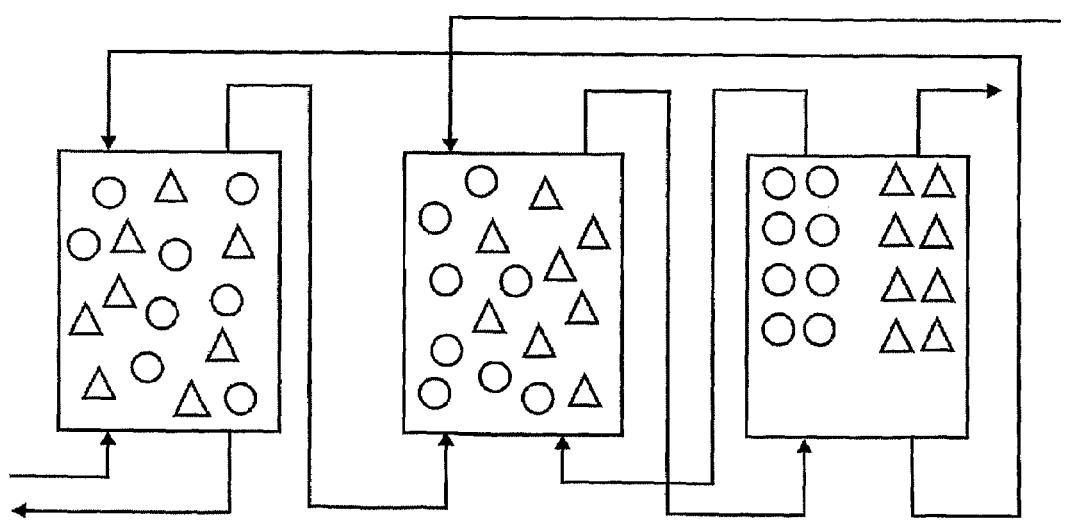

FIG. 3 provides a diagrammatic view of the result obtained from separating the phases, which is achieved by traversing the chambers from left to right.

REFERENCE LIST

1 Chromatography system
2 Chamber
21 Side remote from rotational axes
22 Side near rotational axes
23 Removal site
24 Supply site
3 Liquid carrying connection
31 Inlet
32 Inlet
33 Inlet
34 Inlet
35 Feed inlet
4 Carrier plate
A1, A2, A7, A8 Terminal
B3, B4, B9, B10 Terminal
C5, C6, C11, C12 Terminal
D Rotational axis
U Interruption
R Rotation

The invention claimed is:

1. A continuous countercurrent chromatography system, comprising:
   a plurality of rotating chambers disposed about a rotational axis and configured to receive a liquid or liquid mixture to be examined;
   liquid carrying connections interconnecting individual said chambers to conduct two liquids respectively in countercurrent, wherein one liquid first passes through several chambers and is then returned to respective said chambers first traversed in the current flow direction.

2. The continuous countercurrent chromatography system according to claim 1, wherein said chambers have a first side proximal to the rotational axis and a second side distal from the rotational axis, and wherein a liquid mixture is supplied to said chambers on said first side after having been removed from a chamber lying adjacent on a side opposite the rotational direction on said second side thereof.

3. The continuous countercurrent chromatography system according to claim 1, wherein a liquid mixture is supplied to chambers of a first group at a distal side thereof remote from the rotational axis, after having been removed from a next but one chamber in the rotational direction at a proximal side thereof near the rotational axis.

4. The continuous countercurrent chromatography system according to claim 3, wherein a liquid mixture is supplied to chambers of a second group at a distal side thereof remote from the rotational axis, after having been removed from a chamber lying adjacent in a direction opposite the rotational direction on a proximal side thereof near the rotational axis.

5. The continuous countercurrent chromatography system according to claim 1, wherein said chambers are formed with removal sites and supply sites, and said removal sites and supply sites of a respective said chamber lie on a radial relative to the rotational axis.

6. The continuous countercurrent chromatography system according to claim 1, wherein the two liquids or liquid mixtures are a heavy phase and a light phase.

7. The continuous countercurrent chromatography system according to claim 1, wherein said chambers are interconnected to form an uninterrupted ring.

8. The continuous countercurrent chromatography system according to claim 1, wherein the two liquids are continuously supplied at a respective inlet forming access sites to the interconnected said chambers.

9. The continuous countercurrent chromatography system according to claim 8, wherein said chambers are interconnected to form a chain and wherein a sample substance is supplied between the access sites at another point of the chain of interconnected chambers.

10. The continuous countercurrent chromatography system according to claim 9, wherein the liquid or liquid mixture consists of a solvent or solvent mixture for the sample substance.

11. The continuous countercurrent chromatography system according to claim 1, wherein the liquids are immiscible liquids.

12. The continuous countercurrent chromatography system according to claim 1, wherein said chambers are arranged in a circle.

13. The continuous countercurrent chromatography system according to claim 1, wherein said chambers of said plurality of chambers have an identical structural design.

* * * * *